US00PP09728P

United States Patent [19]

Guillou et al.

[11] Patent Number: Plant 9,728

[45] Date of Patent: Dec. 3, 1996

[54] GERANIUM PLANT NAMED 'GUITOUBLANC'

[76] Inventors: Jacques Guillou, 44, rue Dauphine; Bernard Guillou, 3, Square Henri Colas; Maurice Guillou, 28, rue Ville Pépin, all of 35400 Saint-Malo, France

[21] Appl. No.: 384,528

[22] Filed: Feb. 1, 1995

[51] Int. Cl.[6] ..... A01H 5/00

[52] U.S. Cl. ..... Plt./87.12

[58] Field of Search ..... Plt./87.12

*Primary Examiner*—James R. Feyrer

[57] ABSTRACT

A new and distinct cultivar of geranium plant named Guitoublanc, characterized by its double-type and white flowers that have a pink center; medium-green foliage with brown zonation which forms a ring near the base of the leaf for a maximum of 5 mm; compact plant habit and good branching habit.

1 Drawing Sheet

The present invention comprises a new and distinct cultivar of geranium, botanically known as *Pelargonium peltatum* l'hert, and hereinafter referred to by the cultivar name Guitoublanc.

Guitoublanc is a spontaneous mutation (sport) from the variety Guicerdan that was discovered by the inventors in Saint Malo, Bretagne, France in 1986. In comparison to Guicerdan, the variety Guitoublanc is more compact and the stem of the leaf blade is thicker and a little shorter. In addition, Guicerdan has pink flowers and Guitoublanc has white flowers with a pink center.

The first act of asexual reproduction of Guitoublanc was accomplished when vegetative cuttings were taken from the initial selection in 1987 in a controlled environment in Saint Malo, France by a technician working under the supervision of the inventors. Horticultural examination of selected units initiated in 1990 has demonstrated that the combination of characteristics as herein disclosed for Guitoublanc are firmly fixed and are retained through successive generations of asexual reproduction.

Guitoublanc has not been observed under all possible environmental conditions. The phenotype may vary with variations in environment such as temperature, light intensity and daylength with a change in the genotype of the cultivar. The following observations, measurements, and comparisons describe plants grown in Saint Malo (France) under greenhouse conditions which approximate those generally used in commercial practice.

The following traits have been repeatedly observed and are determined to be basic characteristics of Guitoublanc, which in combination, distinguish this geranium as a new and distinct cultiver:

1. Double-type and white flowers with a pink center.
2. Medium-green foliage.
3. Brown (ca. RHS 200A) zonation which at maximum forms 5 mm from the base of the leaf.
4. Compact plant habit.
5. Good branching habit.

Of the many commercial cultivars known to the inventors, there is no cultivar with which Guitoublanc can be closely compared.

The accompanying photographic drawings show typical flower and foliage characteristics of Guitoublanc.

Figure 2:
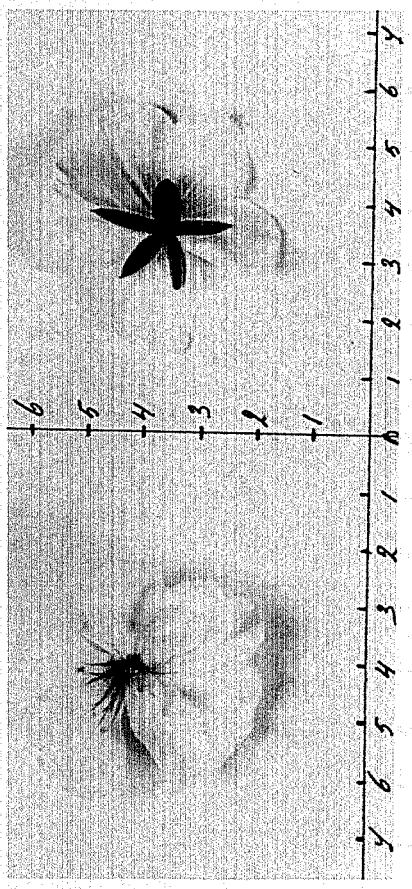
FIG. 2 is a top and bottom view of an individual flower from Guitoublanc.
Figure 3:
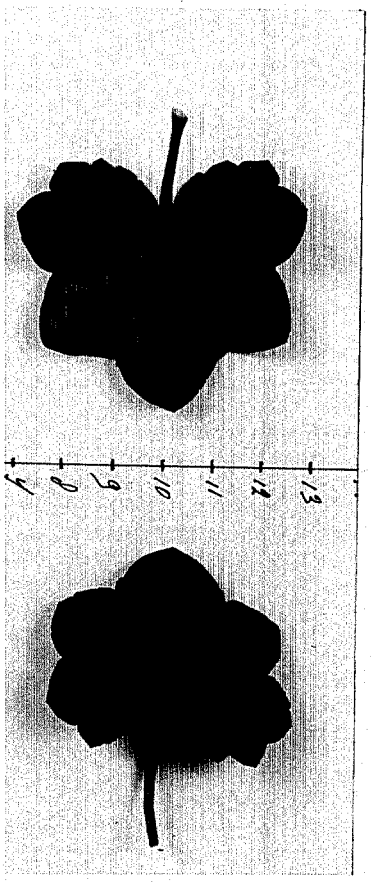
FIG. 3 is a top and bottom view of an individual leaf from Guitoublanc.
Figure 1:
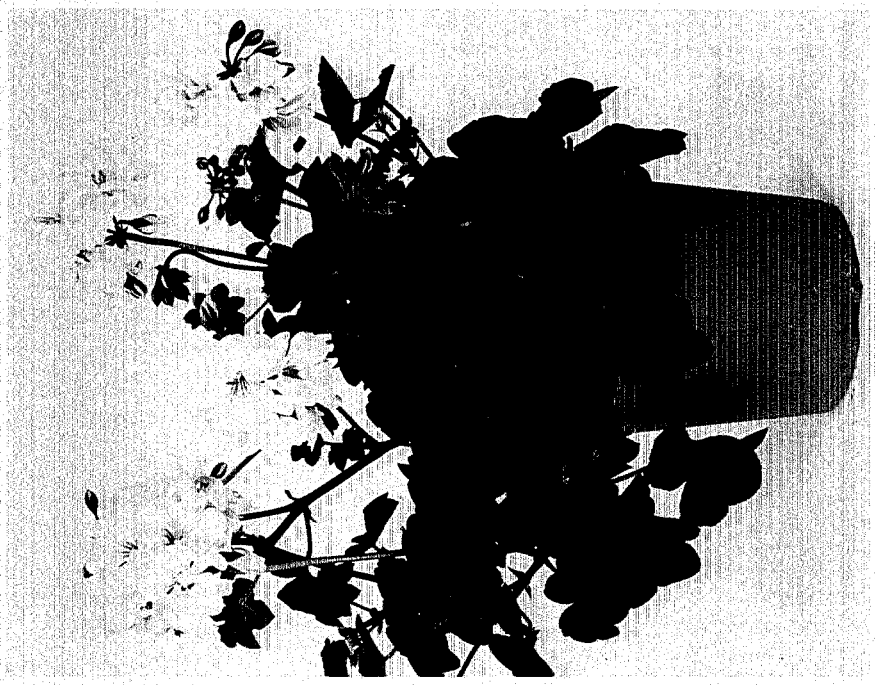
FIG. 1 is a side view of the cultivar.

In the following description, color references are made to the Royal Horticultural Society (RHS) Colour Chart.

Classification:

*Botanical.*—*Pelargonium peltatum* l'Hert cv. Guitoublanc.

*Commercial.*—Ivy geranium. Guitoublanc.

INFLORESCENCE

A. Umbel: Nearly semi-spherical with 6 to 9 buds per umbel.
- *Average diameter.*—80 mm.
- *Average depth.*—42 mm.
- *Peduncle length.*—80 mm.
- *Pedicel length.*—21 mm.

B. Corolla:
- *Average diameter.*—40 mm.
- *Form.*—Double with 10 to 15 petals per flower. There are more petals in the spring than fall.
- *Color (upper surface).*—White with a pink center.
- *Color (margin of upper surface).*—White, RHS ca. 155D.
- *Color (center of upper surface).*—RHS ca. 58C, red purple group, with dark-red veins.
- *Color (lower surface).*—White with light pink veins near center.
- *Sepal number.*—5.

C. Bud: Elliptic.
- *Color (abaxial).*—Green, no anthocyanin.
- *color (adaxial).*—Bright pink that is similar in color to the center of the flower, red-purple group 58C.

D. Reproductive organs:
- *Androecium.*—3–7 fertile anthers, white filaments, orange pollen.
- *Gynoecium.*—5–6 lobed stigma, pink style and stigma.

E. Spring flowering response period: 1.6 flowers per umbel opened 15 weeks after planting of unrooted cuttings (pinched plants).

F. Outdoor flower production: 80–90 umbels per plant from late April/May through October. Pinching of spent blooms is necessary to ensure continued flowering.

G. Durability: Shatter resistance good.

PLANT

A. Foliage:
- *Form.*—Ivy shaped.
- *Base.*—Closed to party overlapping.
- *Color (abaxial).*—Medium-green (RHS 139A).
- *Color (adaxial).*—Green.
- *Color (zonation).*—Brown (ca. RHS 200A), at maximum 5 mm from the base of the leaf.

B. General appearance and form:

*Internode length.*—30 to 40 mm.

*Branching pattern.*—5–6 branches per plant.

*Height.*—50–60 cm. in August.

*Plant vigor.*—the plant grows vigorously producing many leaves and flowers.

C. Tolerance to Botrytis: Good.

What is claimed is:

1. A new and distinct cultivar of geranium plant named Guitoublanc, as illustrated and described.

* * * * *